United States Patent

Barber

[11] Patent Number: 5,266,806
[45] Date of Patent: Nov. 30, 1993

[54] TRANSMISSION DAMAGE TESTER
[75] Inventor: Daniel D. Barber, Tustin, Calif.
[73] Assignee: OCA Applied Optics, Inc., Garden Grove, Calif.
[21] Appl. No.: 735,855
[22] Filed: Jul. 25, 1991
[51] Int. Cl.$^5$ ............... G01N 21/47; G01N 21/88
[52] U.S. Cl. .................... 250/341; 356/239
[58] Field of Search .......... 250/572, 563, 338.1, 250/340, 341; 356/237, 239, 445–448, 432, 382, 387

[56] References Cited

U.S. PATENT DOCUMENTS 4,455,086  6/1989  West et al. ................ 280/572
5,072,128  12/1991 Hayano et al. ............. 356/237

Primary Examiner—Vincent P. McGraw
Assistant Examiner—K. P. Hantis
Attorney, Agent, or Firm—Joseph R. Dwyer

[57] ABSTRACT

A method and apparatus for determining the transmission capability of a substrate and any damage which may affect said transmission capability comprising directing a focused infrared illumination beam through the substrate and observing the reflected or scattered light to detecting any scratch, fracture, blemish or the like in the substrate surface, or within the substrate itself, by detecting any change in the energy level of the sensed beam or change in reflected scattered light. The illumination beam provides a spot on the substrate surface and, by mapping an entire substrate of said spots adjacent one another and comparing the energy or light level of adjacent spots, any internal or external damage can be determined. A portable battery operable tester with an illumination beam and associated optics and a transmitted beam and associated optics enables such detection of transmission loss. The apparatus may alternately include a single infrared focused illumination beam and a beam splitter to detect any transmission loss in the substrate. The apparatus may alternately include an illumination beam and means for detecting scattered light as a function of transmission loss of the substrate.

16 Claims, 10 Drawing Sheets

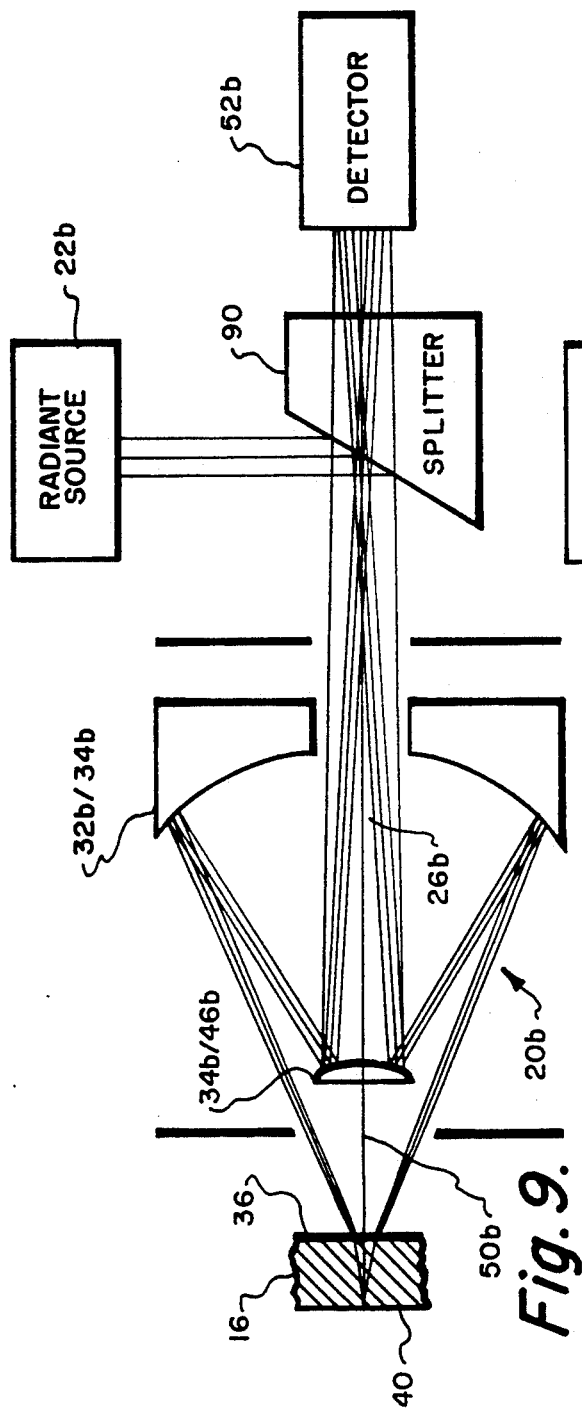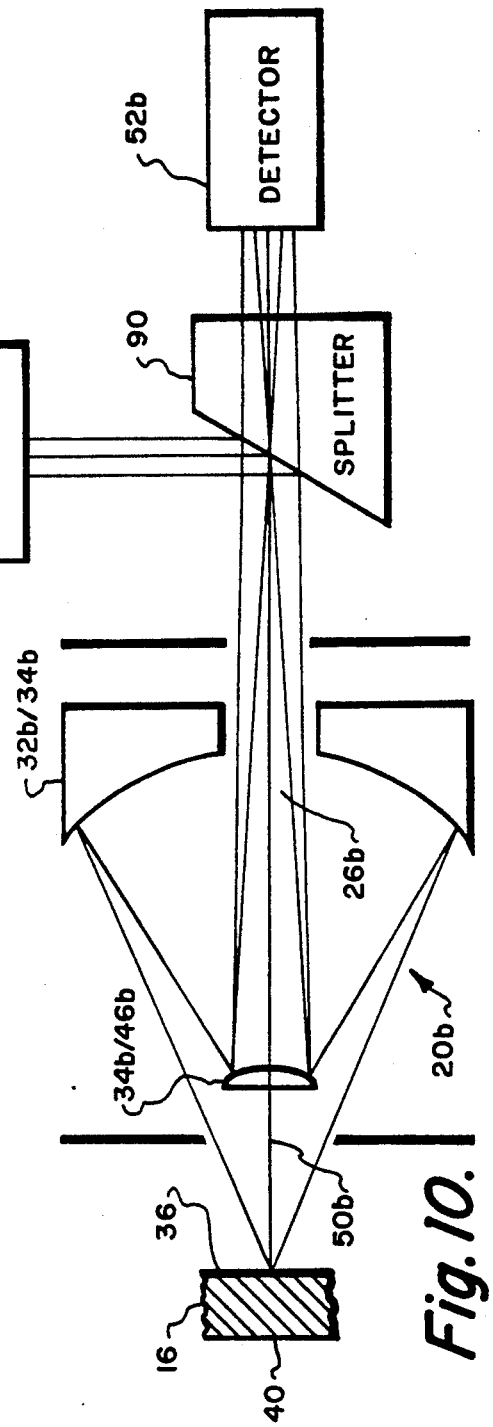

TRANSMISSION DAMAGE TESTER

BACKGROUND OF THE INVENTION

This invention relates to a method and apparatus for testing the ability of a substrate to transmit infrared radiation and is specifically directed to a method and apparatus for testing the ability of domes and windows of missiles and aircraft to transmit infrared radiation.

"Substrate" as used herein means the wall, or bulk material, which forms the dome or window and which has a first or outer surface and a second or inner surface and, while curved substrates are shown and discussed throughout, this invention will also test planar substrates.

The successful operation of a missile or an aircraft in identifying an object emitting infrared radiation depends upon the ability of its dome and/or window to transmit the received radiation therethrough and any loss in transmission in the substrate due to rain, sand and flying particles which damage the substrate and cause erosion, scratches, fractures and the like may increase the probability of failure of the missile or aircraft to perform its mission. Current requirements demand replacement of the dome or window if more than 4% in transmission loss has been detected.

Current methods of inspecting and testing these substrates for damage include a visual examination of the substrate surfaces or impinging the substrate surfaces with light and measuring the backscatter as a function of cracks or scratches on the inspected surfaces.

One problem with the current methods is the assumption that a fracture or a defect within the substrate will have a signature on the outer surface which can be detected. It has been found, however, that a fracture or defect within the substrate itself, ie, between the inner and outer surfaces, may not necessarily have a signature on the outer surface and the current methods will not detect such a fracture or defect.

Another problem with the current methods of testing substrates is that an undetected fracture or defect within the substrate may propogate to the surface of a substrate during flight operation and may cause a loss of transmission, or possibly the destruction of the dome or window, resulting in a failure of the missile or aircraft.

It is therefore an object of this invention to improve testing for transmission loss in a substrate by providing a means for testing not only the substrate surfaces for cracks, scratches, blemishes and the like but also within the substrate itself.

It is also another object of this invention to provide a method and apparatus for testing for transmission loss in a substrate and damage or defects within the substrate which may result in transmission loss or fracture and loss of the substrate resulting in loss of the airborne vehicle during flight.

SUMMARY OF THE INVENTION

The method and apparatus which accomplishes the foregoing objects comprises directing a focused infrared illumination beam through the substrate and observing the reflected or scattered light to detect any scratch, fracture, blemish or the like in the substrate surface or within the substrate itself by detecting any change from the expected scatter light level or change in the energy level of the reflected beam. The illumination beam provides a spot or footprint on the substrate surface and, by mapping an entire substrate of said spots adjacent to one another and comparing the reflected scattered light or energy level of adjacent spots, any internal or external damage of the substrate can be determined.

A portable type battery operable tester with an illumination beam and associated optics and a transmitted beam and associated optics enables such detection of transmission loss in domes and windows already mounted in missiles and aircraft and may be used on the deck of a ship or in a hangar environment, and provides a go-or-no-go quick evaluation of the dome or window for replacement due to transmission loss.

Instead of the two beams and separate optics, a single infrared focused illumination beam may be used with a beam splitter to detect any disruption of the reflected beam from normal which will indicate damage to the substrate.

Also, instead of either of the foregoing, the tester may include an illumination beam and means for detecting scattered reflected light.

BRIEF DESCRIPTION OF THE DRAWINGS

FIG. 9 illustrates the testing for defects within a substrate by a single illumination beam (common mode), FIG. 10 illustrates the testing for defects externally of the substrate by a single illumination beam (common mode)

DETAILED DESCRIPTION

Figure 1:
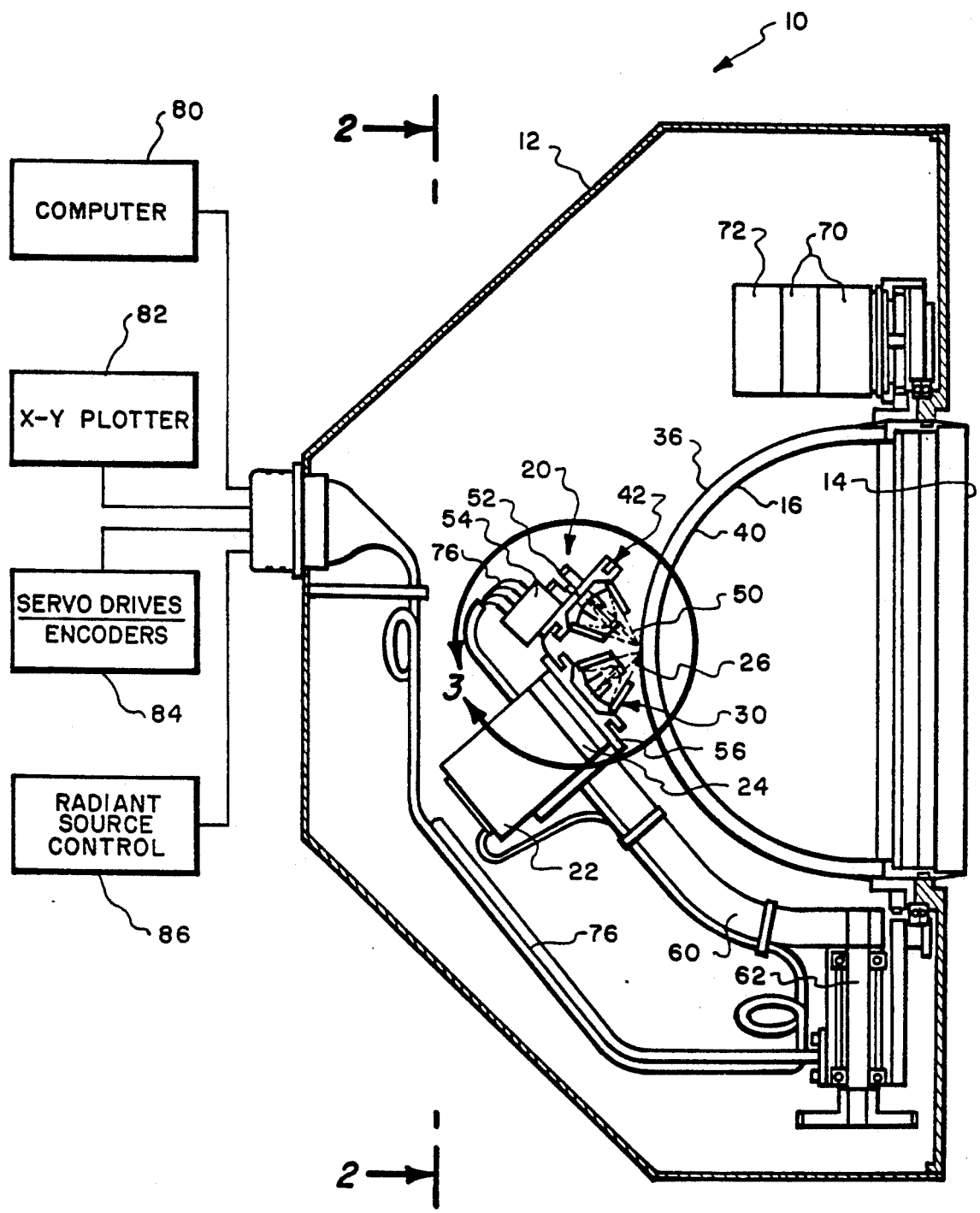
FIG. 1 is an elevational view, in cross section, of the transmission damage tester of this invention shown testing a dome.
Figure 2:
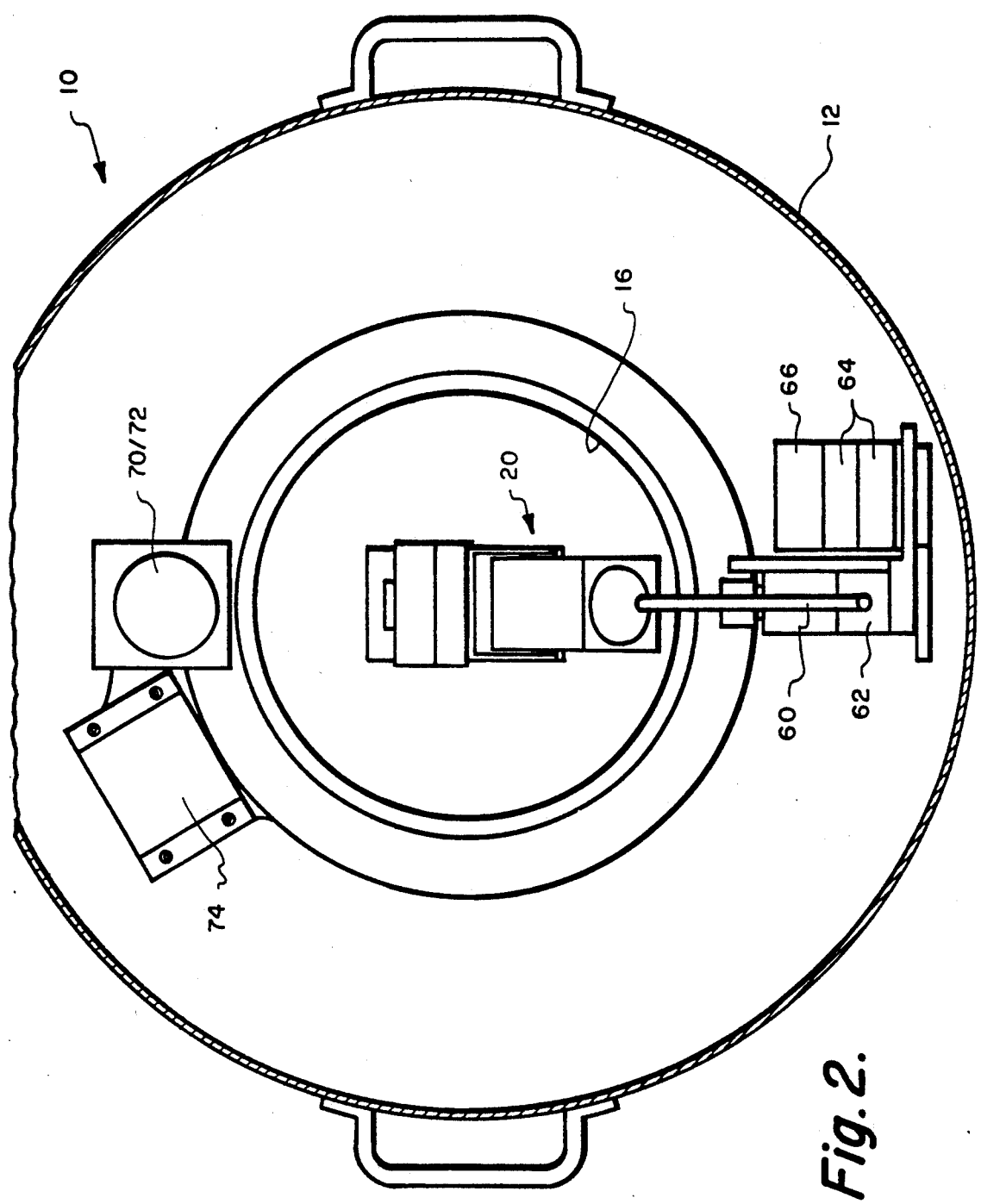
FIG. 2 is an elevational view taken along 2—2 of FIG. 1.
Figure 3:
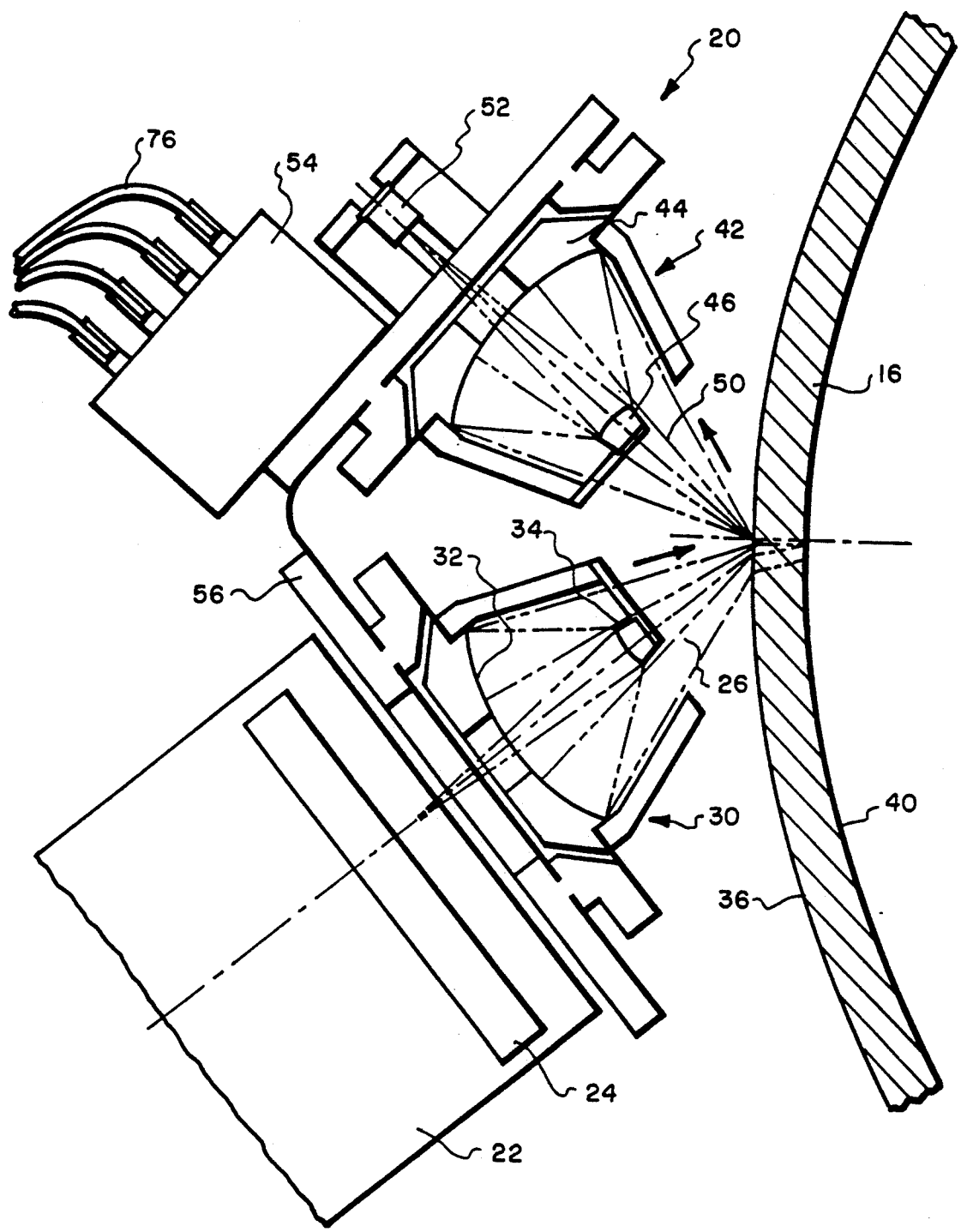
FIG. 3 is an enlarged view of the area encircled in FIG. 1 as an optical diagram of illumination receiver optics.

FIGS. 1-3 show the transmission damage tester 10 of this invention which includes a housing 12 with an opening 14 in which a substrate 16 in the form of a dome, typically coated, is positioned for testing. The size of the opening 14 will vary according to the substrate being tested, whether a window or dome.

Within the housing 12 is beam source/sensor head 20 which comprises an IR source 22 (black body) for IR radiation in the 2-12 micron wavelength and a chopper 24 for generating an IR illumination beam 26 which is focused by an optical system 30 shown as a reflective optic with a primary optic 32 and a secondary optic 34. The illumination beam 26 impinges the outer surface 36 of the substrate 16 under test where it is refracted onto the inner surface 40 and reflected back to the outer surface 36. The head 20 also includes a receiver optical system 42 shown as a reflective optic with a primary optic 44 and a secondary optic 46 focused onto the outer surface 36 to receive and direct a transmitted beam 50 to a detector 52 with a preamplifier 54. The head 20 includes a mounting bracket 66 and is mounted for 180° movement on a gimbal arm 60 of a gimbal 62. The gimbal arm 60 is moved horizontally by an azimuth motor/gearhead 64 and the position of the head 20 is detected by an azimuth encoder 56. Similarly, the head 20 is mounted for 180° elevational movement by an elevational motor/gearhead 70 and the position of the head 20 is detected by an elevational encoder 72. The gimbal 62 is rotated by elevational motor/gearhead 70 and together with the azimuth motor/gearhead 64 hemispherical testing of the dome by the head 20 is accomplished.

Also shown in these figures is a temperature controller 74 for the black body IR source 22 and suitable cables 76 for connecting the head 20 to a computer 80, X-Y plotter 82, servo drive and position encoder information 84, radiant source control 86 and such other equipment as necessary or desirable.

As shown more clearly in FIG. 3, the IR illumination beam 26 is directed onto the outer surface 36, which is nearest the beam source 22, and through the substrate 16 and reflected back as transmitted beam 50 to be detected by the detector 52. The head 20 produces a series of eliptical or circular spots (footprints) adjacent one another, and the location of each spot is known by the information gathered from the encoders 66 and 72 and recorded on the X-Y plotter 82. Thus, a map of the entire hemisphere is provided and the data gathered by the detector 52 will indicate the transmission capability of the substrate at each spot. If the substrate is undamaged, or contains no flaw, the radiant energy level of the transmitted beam 50 transmitted to the detector 52 will be substantially uniform throughout the hemisphere. However, if the substrate is damaged in any way, adjacent spots will indicate a loss in transmission capability of the substrate by the measured change in radiant energy in the transmitted beam 50, or by the measured scattered light 50a as detected by the detector 52. By comparing such spots throughout the entire hemisphere, any flaw can be identified.

Figure 4:
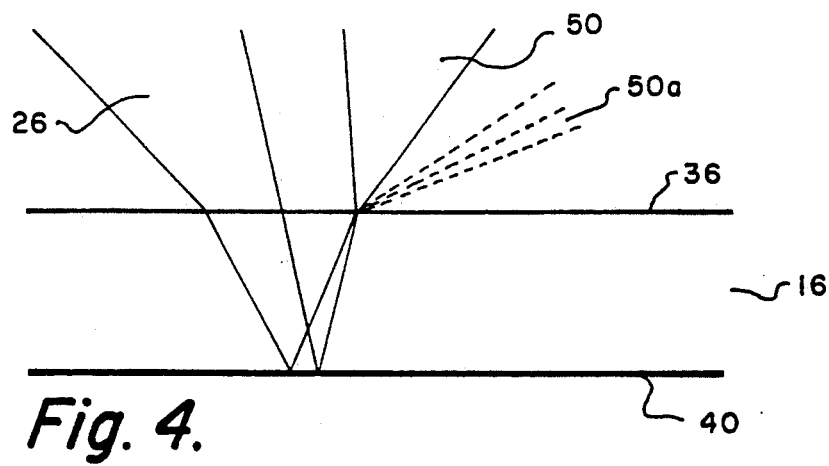
FIG. 4 is a partial view of the illumination beam and the transmitted beam on an undamaged surface or without damage within the substrate itself.

FIG. 4 shows the illumination beam 26 directed through the outer surface of the substrate and reflected off the inner surface. The transmitted beam 50 is then focused on the outer surface as the transmitted light exits from the undamaged substrate. As shown in this figure, the measured transmission beam 50, or the scattered light 50a will be uniform as the illumination beam 50 is scanned over the substrate.

Figure 5:
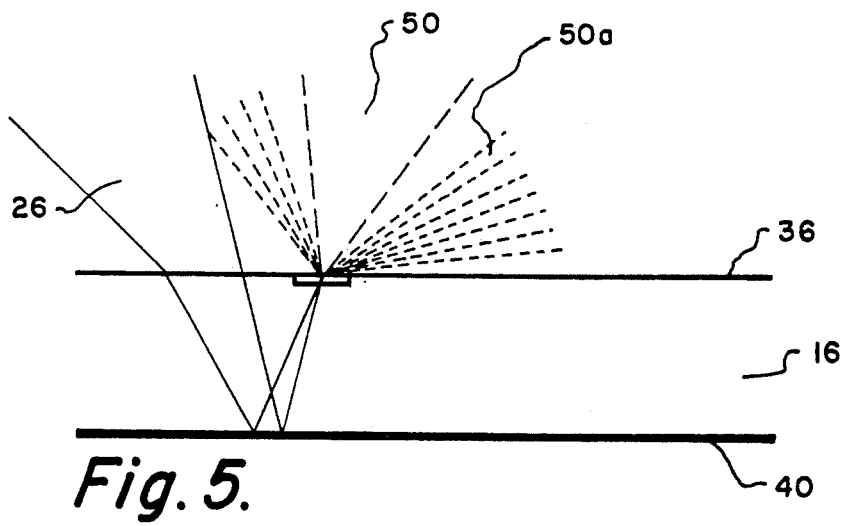
FIG. 5 is a partial view illustrating the identification of damage in the outer surface of the substrate.

FIG. 5 shows the effect a surface damage site will have on the received light level. If the tester 10 is observing the transmission beam 50, the measured light level will be reduced in the vicinity of the surface damaged sites. If the tester is observing the scatter 50a, the light level of the scatter will increase in the vicinity of the damaged sites.

Figure 6:
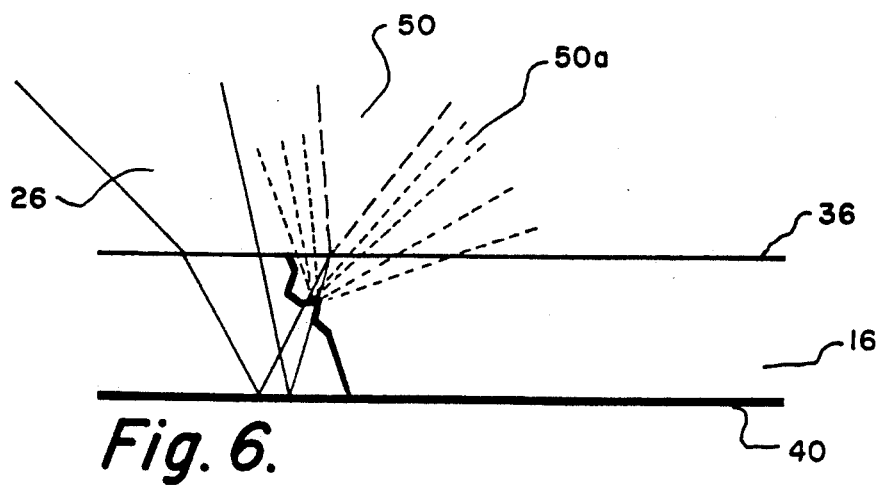
FIG. 6 is a partial view illustrating the identification of damage within the substrate itself.

FIG. 6 shows the effect a subsurface damaged site has on the received beam. The effect on the receiver light level is similar to that discussed for FIG. 5 except that the scatter source is now buried in the substrate.

FIGS. 4-6 also show that the illumination beam need not be precisely focused as shown in FIG. 3 but show what is important is the disruption of the transmitted beam as by loss of transmission capability of the substrate, which will be detected as a loss of radiant energy at a particular spot.

In the following FIGS, those components having the same function as in the previous figures will be given the same reference numeral but with a suffix b to simplify the description thereof.

Figure 7:
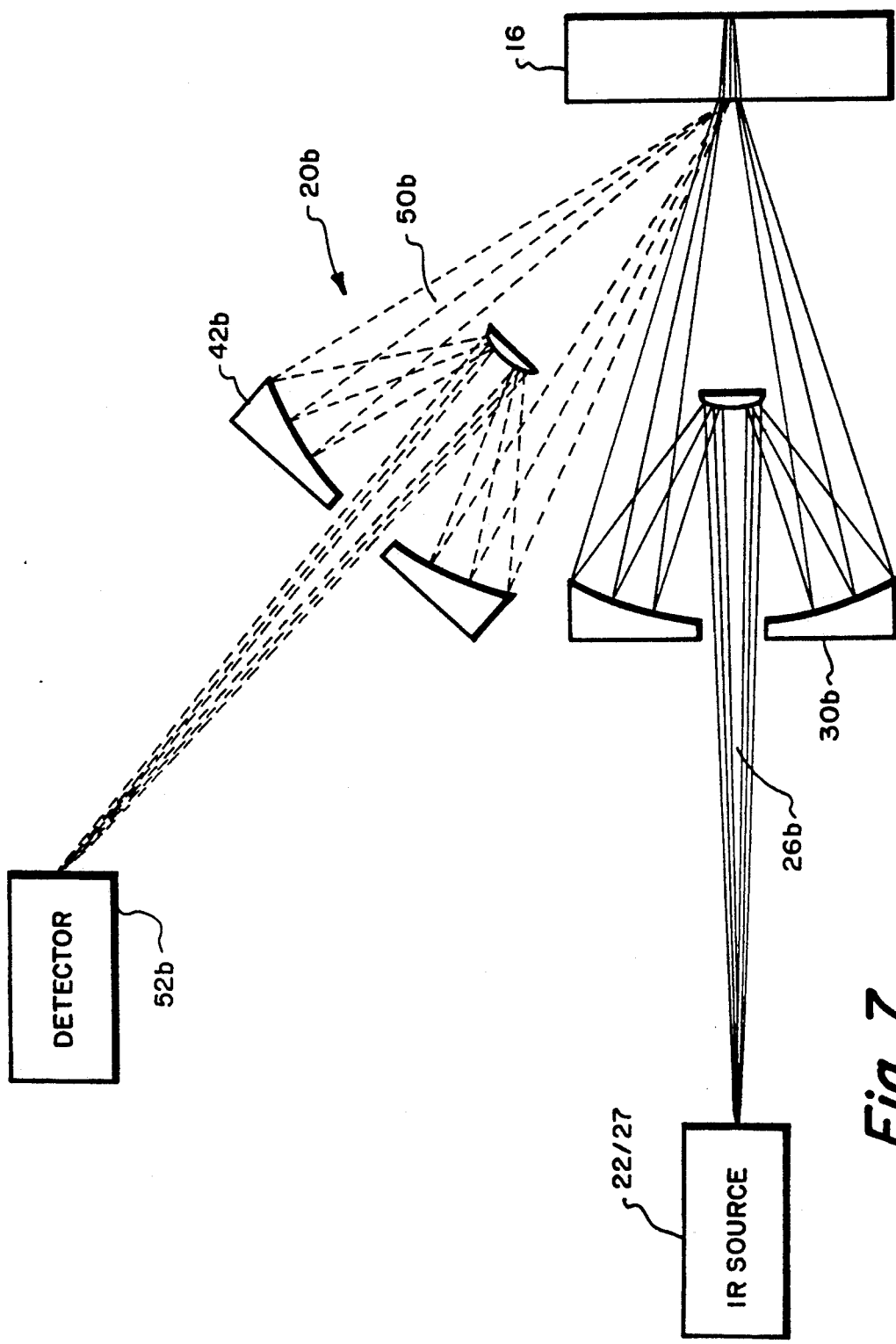
FIG. 7 illustrates testing for defects on the surface or within a substrate by measuring the scattered light caused by such defects.

Another configuration of the tester 10 is to measure the scattered light 50a rather than the transmitted light as shown in FIGS. 4, 5, and 6. In FIG. 7, the illumination beam 26b is directed normal to the substrate and the receiver optic 42b in this tester is located to receive light scattered away from the specular reflection angle. This is the inverse of the transmission measurement in that a defect in the substrate would increase the scattered light level whereas such a defect would decrease the transmitted light level.

The capability to discern between surface damage and subsurface damage could be added to a scatter measurement detector by including several detectors in the receiver which look at the location of the scatter source over the thickness of the substrate. Two such detectors 42b are shown in FIG. 8.

FIG. 9 illustrates a reflective optic 32b/34b for directing a single IR beam 26b (common mode) through the outer surface 36 of the substrate 16 which is reflected back onto a beam splitter 90 as a separate beam 50b. Any change in the transmission capability of the substrate due to a blemish or defect on the surfaces 36 or 40, or within the substrate, will disrupt beam 50b impinging on the beam splitter 90 and will be sensed by detector 52b.

FIG. 10 illustrates the same reflective optic 32b/34b except that the beam 26b is focused on the external surface 36 so that any damage on the external surface 36 will produce a change in the reflected beam 50b which will be identified by the beam splitter 90 and directed to detector 52b.

Figure 8:
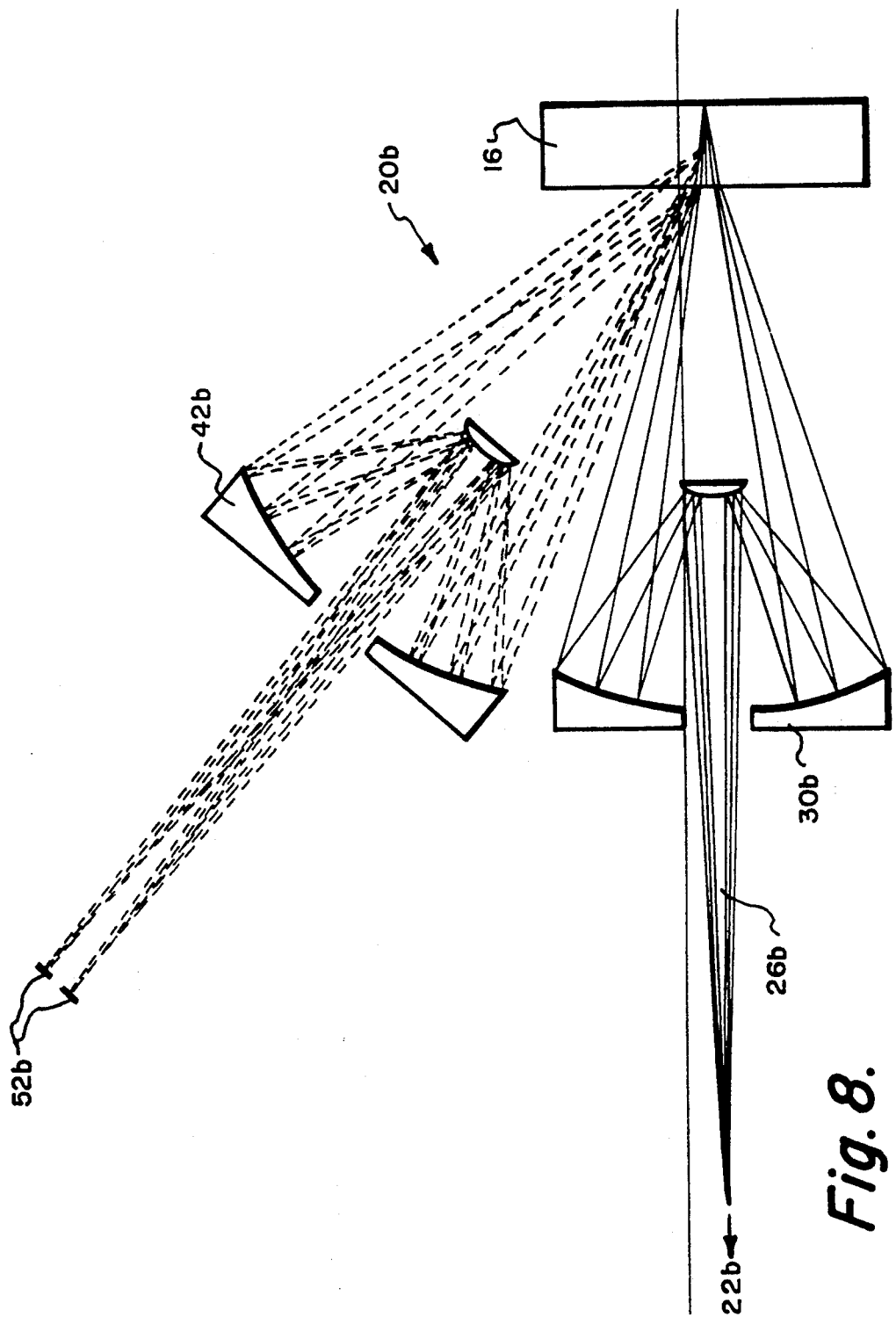
FIG. 8 illustrates testing for defects as in FIG. 7 but with additional means for measuring scattered light.

The head 20b with the means for detecting scattered light as in FIGS. 7 and 8 or the head 20b with the single reflective optical system as in FIGS. 9 and 10 may be substituted for the double beam optical head 20 of FIGS. 1-5.

Figure 11:
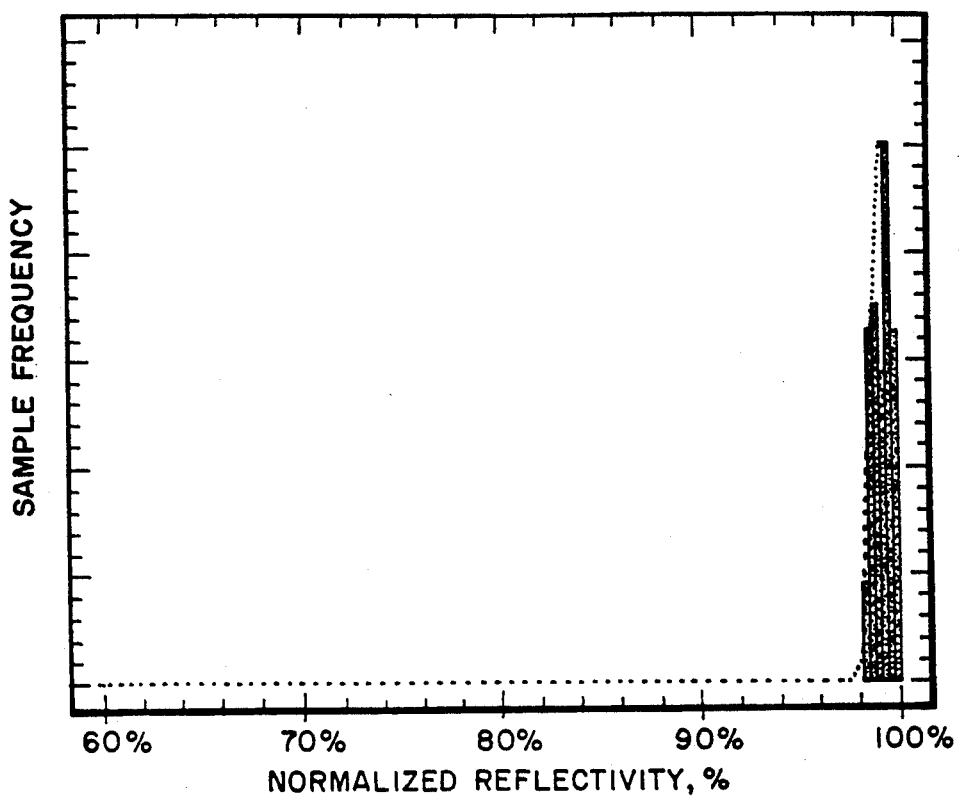
FIG. 11 is a histogram of surface transmission measurement using reflection off the internal surface of an undamaged sample.

FIG. 11 is a histogram of samples taken in a raster scan of an undamaged one inch diameter window. The sample set consists of greater than 2000 samples. The figure depicts the sample frequency as a function of the measured normalized (relative to peak) reflectivity. It shows that for an undamaged part, the samples fall into a very narrow band between 98 and 100% of the peak measurement.

Figure 12:
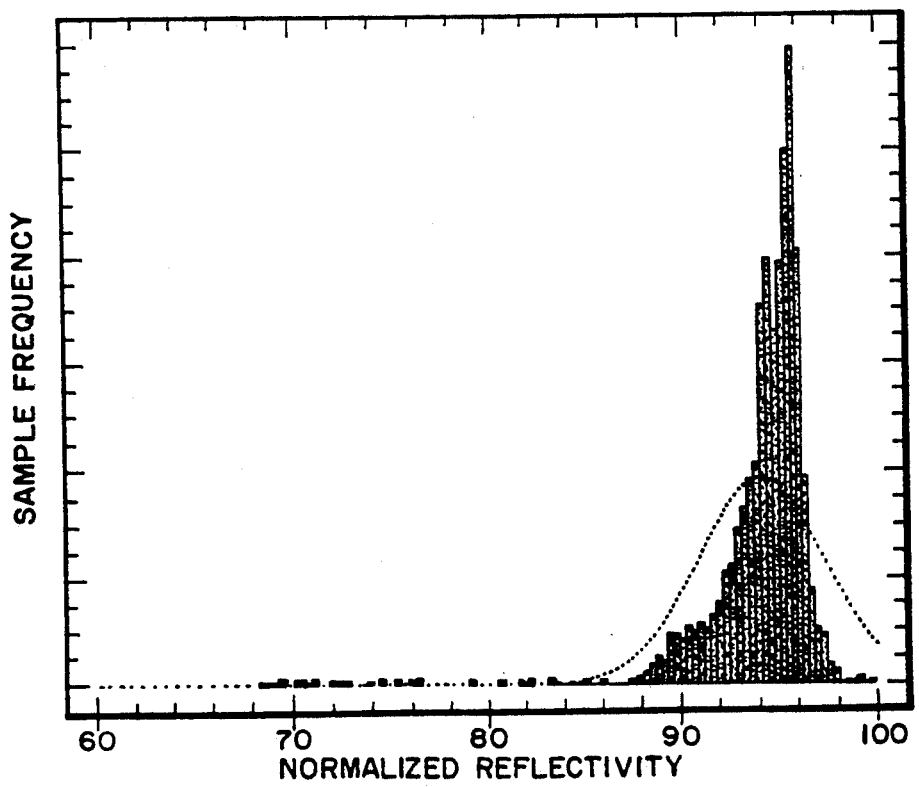
FIG. 12 is a histogram of external surface reflectivity measurement of a fractured sample.
Figure 13:
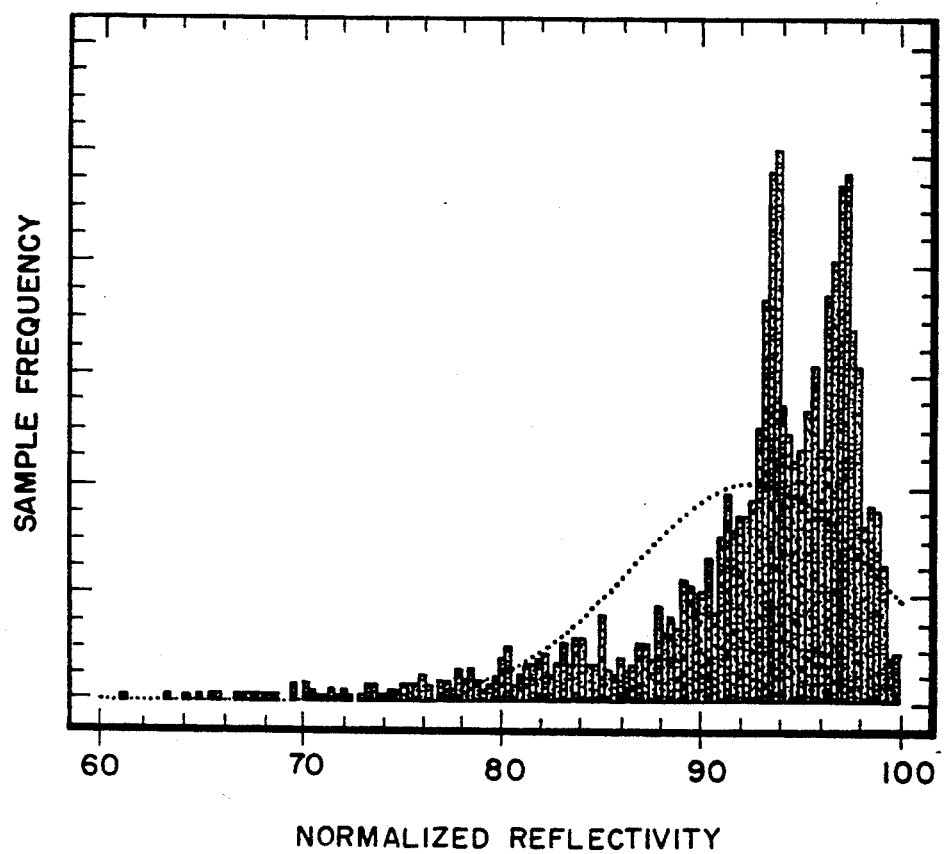
FIG. 13 is a histogram of internal reflectivity measurement of the same sample substrate.

FIG. 12 shows a histogram similar to that described above taken from a damaged sample. This data was taken looking at the external surface reflection. FIG. 13 is another histogram for the same damaged sample using internal reflection.

Essentially, FIG. 13 as compared to FIG. 12, illustrates the significant difference in the system where a fracture is precisely identified in FIG. 13 and only vaguely characterized in FIG. 12. The test represented in FIG. 12 can be said to be essentially a backscattering technique as in the prior art.

Figure 14:
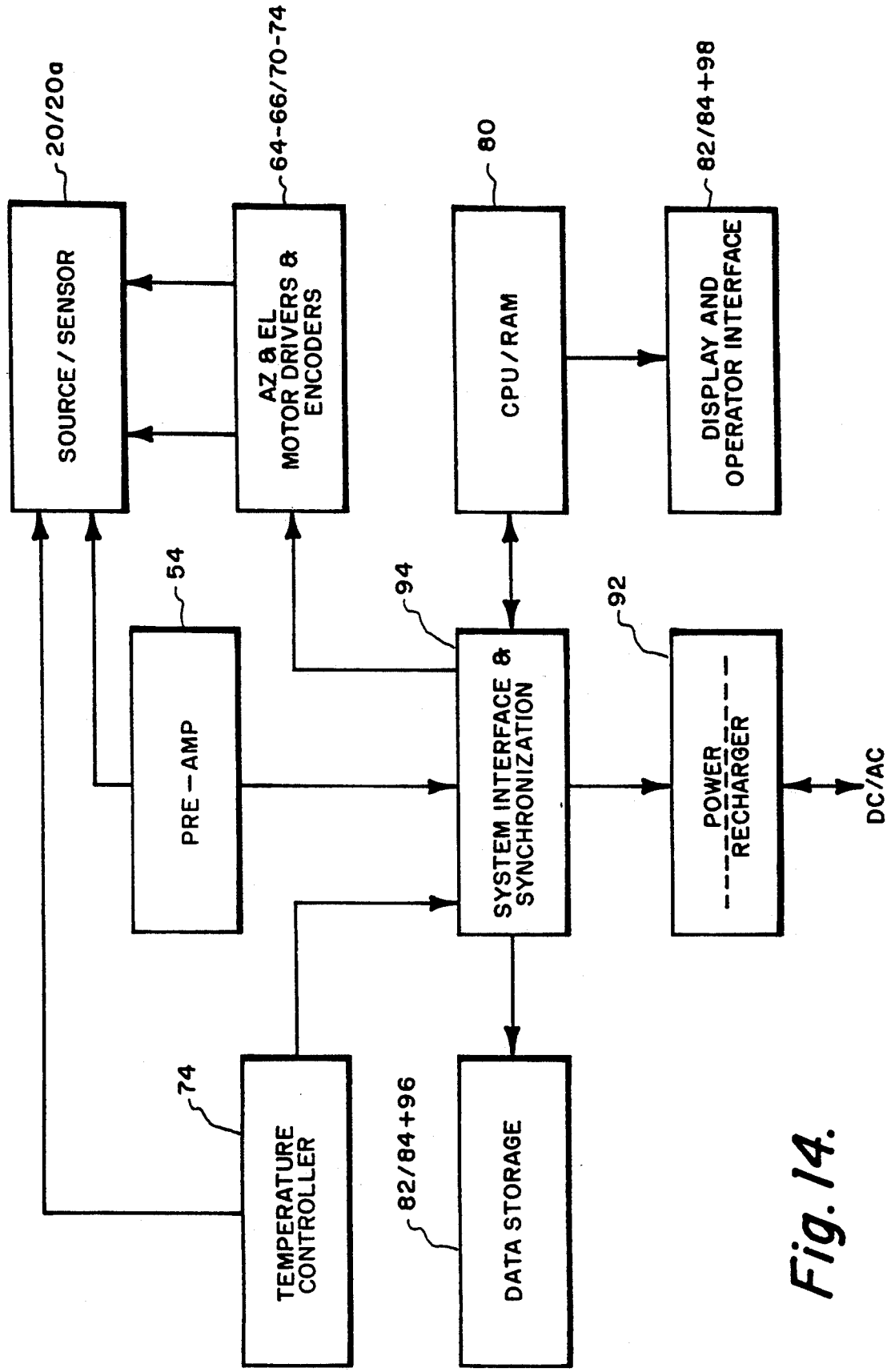
FIG. 14 is a typical block diagram for the transmission damage tester of this invention with additional optional equipment.

FIG. 14 is a schematic block diagram of a circuit useful in the foregoing devices and where appropriate the reference numerals corresponding to the component of the foregoing devices identify the block diagram. The circuit also includes a power source 92 and system interface and synchronization circuitry 94 and optional items such as a data storage means 96 and a display and operator interface means 98.

I claim:

1. A method of determining the transmission capability of a substrate and determining any damage which may effect such transmission capability comprising the steps of:
   providing an infrared source,
   focusing said infrared source as an illumination beam onto a first surface of said substrate and through the material forming said substrate to a second surface of said substrate where said beam is reflected back through said first surface as a transmitted beam forming an illuminated spot on said first surface,
   receiving said transmitted beam in a detector which measures the radiant energy level of said spot relying solely on the energy from said spot as formed by said transmitted beam to determine the transmission capability of said substrate.

2. The method as claimed in claim 1 including forming a plurality of said spots adjacent to one another and measuring the changes in energy level of the transmitted beam as a function of any damage on the surfaces or within said substrate.

3. A method of determining the transmission capability of a substrate and determining any damage which may effect such transmission capability comprising the steps of:
   providing an infrared source,
   focusing said infrared source as an illumination beam onto a first surface of said substrate and through the material forming said substrate to a second surface of said substrate where said illumination beam is reflected back through the substrate as an illuminated path to the first surface exiting as a focused illuminated spot on said first surface such that anywhere in the illuminated path, scattered light can be generated by substrate defects,
   receiving said scattered light in at least one detector which measures the amount of said scattered light emanating from said defects.

4. the method as claimed in claim 3 further including forming a plurality of said spots adjacent one another and measuring the changes in the reflected scattered light level as a function of any damage on the surfaces or within said substrate.

5. The method as claimed in claim 3 further including a plurality of detectors surrounding said scattered light, each of which measures the amount of scattered light emanating from said spot.

6. An apparatus for measuring the transmission capabilities and defect characteristics of a substrate, such as a dome or window, of an airborne vehicle comprising:
   an infrared source,
   means for focusing said infrared source as a beam on and through an outer surface and through the material forming said substrate and reflecting said beam off an inner surface of said substrate whereupon the beam returns to the first surface exiting as it focuses on the surface as a transmitted beam,
   means for receiving the transmitted beam from said substrate,
   means for detecting the energy level of said transmitted beam as a function of the transmission capability of the substrate, said detecting means relying solely on said transmitted beam energy level.

7. The apparatus as claimed in claim 6 wherein said means for focusing said infrared source comprises a reflective optical system and the means for receiving the transmitted beam comprises a reflective optical system.

8. The apparatus as claimed in claim 7 wherein said means for focusing said beam and for receiving said transmitted beam comprises a single reflective optical system with a beam splitter to detect said transmitted beam.

9. The apparatus as claimed in claim 7 including means for moving both said reflective optical systems so as to focus said beam and to receive the transmitted beam from said substrate on many areas over the entire substrate.

10. An apparatus for measuring the transmission capability of a substrate comprising:
    means for positioning said substrate for testing,
    a beam source/sensor head including,
      an infrared source which emits a beam of infrared radiation,
      means for focusing said beam as a transmitted beam on a first surface of said substrate near said infrared source and through said substrate so as to be refracted within said substrate and reflected back off a second surface of said substrate and back through said first surface as a transmitted beam and forming a spot on said first surface,
      means for detecting said transmitted beam and determining the radiation level of said transmitted beam as a function of the transmission capabilities of the substrate at said spot, said detecting means relying solely on the reflected energy off said second surface.

11. The apparatus as claimed in claim 10 further including means for moving said beam source/sensor head relative to the entire area of said substrate to determine the radiation level at each adjacent spot on said substrate and determining the difference in radiation levels at adjacent spots as a function of the loss of transmission capability of said substrate.

12. An apparatus for measuring the transmission capabilities of a substrate of an airborne vehicle comprising:
    an infrared source,
    means for focusing the infrared source as an illumination beam on the outer surface of said substrate and through the material forming said substrate and reflecting said illumination beam off the inner surface of said substrate, and
    means for receiving and measuring a light level of any scattered light reflected off said substrate as a function of the transmission capability of the substrate.

13. The apparatus as claimed in claim 12 wherein said means for receiving and measuring the light level of said scattered light comprises detector means.

14. The apparatus as claimed in claim 13 including a plurality of detector means.

15. The apparatus as claimed in claim 14 further including means for moving said illumination beam across an entire substrate for comparing the level of scattered light throughout the entire substrate as a function of transmission loss of said substrate.

16. The apparatus as claimed in claim 14 wherein said plurality of detector means includes means for determining whether the scattered light is from a defect on one of the surfaces or within the material forming the substrate.

* * * * *